United States Patent [19]

Schmitt

[11] Patent Number: 5,689,024

[45] Date of Patent: Nov. 18, 1997

[54] USE OF CRYSTALLINE SUZ-9

[75] Inventor: Kirk D. Schmitt, Pennington, N.J.

[73] Assignee: Mobil Oil Corporation, Fairfax, Va.

[21] Appl. No.: 347,917

[22] Filed: Dec. 1, 1994

Related U.S. Application Data

[63] Continuation-in-part of Ser. No. 253,992, Jun. 3, 1994, Pat. No. 5,399,337.

[51] Int. Cl.$^6$ .............. C07C 2/54; C07C 7/12; C10G 11/05; C10G 35/095
[52] U.S. Cl. .............. 585/467; 585/722; 585/739; 585/820; 208/113; 208/120; 208/134; 208/136; 208/137; 208/138; 210/690; 210/691; 568/791
[58] Field of Search .............. 208/113, 120, 208/134, 136, 137, 138; 585/446, 467, 709, 722, 734, 739, 820; 568/790, 791, 794; 210/660, 690, 691

[56] References Cited

U.S. PATENT DOCUMENTS

| | | | |
|---|---|---|---|
| 3,758,403 | 9/1973 | Rosinski et al. | 208/120 |
| 3,950,496 | 4/1976 | Ciric | 423/328 |
| 4,309,280 | 1/1982 | Rosinski et al. | 208/120 |
| 4,430,199 | 2/1984 | Durante et al. | 208/114 |
| 4,454,241 | 6/1984 | Pine et al. | 502/68 |
| 4,498,975 | 2/1985 | Pine et al. | 208/114 |
| 4,567,152 | 1/1986 | Pine | 502/64 |
| 4,584,091 | 4/1986 | Pine | 208/114 |
| 4,765,884 | 8/1988 | Walker et al. | 208/89 |
| 4,873,211 | 10/1989 | Walker et al. | 502/64 |
| 4,927,523 | 5/1990 | Donnelly | 208/120 |
| 4,970,183 | 11/1990 | Nakamoto et al. | 502/68 |
| 4,994,424 | 2/1991 | Leib et al. | 502/41 |
| 5,082,815 | 1/1992 | Macedo | 502/41 |
| 5,110,776 | 5/1992 | Chitnis et al. | 502/64 |
| 5,126,298 | 6/1992 | Absil et al. | 502/68 |
| 5,397,561 | 3/1995 | Smith | 423/704 |

FOREIGN PATENT DOCUMENTS 0 526 252 A1   2/1993   European Pat. Off. .

*Primary Examiner*—Glenn A. Caldarola
*Assistant Examiner*—Walter D. Griffin
*Attorney, Agent, or Firm*—Peter W. Roberts; Malcolm D. Keen

[57] ABSTRACT

This invention relates to use of a new and improved form of crystalline material identified as having the structure of SUZ-9 as a sorbent or a catalyst for organic compound, e.g., hydrocarbon compound, conversion.

36 Claims, 1 Drawing Sheet

USE OF CRYSTALLINE SUZ-9

CROSS-REFERENCE TO RELATED APPLICATIONS

This is a continuation-in-part of application Ser. No. 08/253,992, filed Jun. 3, 1994, now U.S. Pat. No. 5,399,337.

BACKGROUND OF THE INVENTION

1. Field of the Invention

This invention relates to use of an improved form of crystalline material identified as having the structure of SUZ-9 as a catalyst component for organic compound, e.g., hydrocarbon compound, conversion, or as a sorbent.

More particularly, this invention relates to use of crystalline SUZ-9 synthesized in a particular new way to yield SUZ-9 of high purity, improved sorbent properties, and enhanced catalytic utility.

2. Discussion of the Prior Art

Porous inorganic solids, both natural and synthetic, have been demonstrated in the past to have catalytic properties for various types of hydrocarbon conversion and as separations media for industrial applications. Certain zeolitic materials are ordered, porous crystalline silicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of large dimensions, these materials have come to be known as "molecular sieves" and are utilized in a variety of ways to take advantage of these properties.

Such molecular sieves, both natural and synthetic, include a wide variety of positive ion-containing crystalline silicates. These silicates can be described as rigid three-dimensional frameworks of $SiO_4$ and $AlO_4$ in which the tetrahedra are crosslinked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example, an alkali metal or an alkaline earth metal cation. This balanced electrovalence can be expressed by a formula wherein the ratio of aluminum to the number of various cations, such as Ca/2, Sr/2, Na, K, or Li is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. These zeolites have come to be designated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); and zeolite ZSM-12 (U.S. Pat. No. 3,832,449), merely to name a few.

Although the term "zeolites" encompasses materials containing silica and alumina, it is recognized that the silica and alumina portions may be replaced in whole or in part with other oxides. More particularly, $GeO_2$ is an art-recognized substitute for $SiO_2$. Also, $B_2O_3$, $Cr_2O_3$, $Fe_2O_3$, and $Ga_2O_3$ are art-recognized replacements for $Al_2O_3$. Accordingly, the term "zeolite" as used herein shall connote not only materials containing silicon and, optionally, aluminum atoms in the crystalline lattice structure thereof, but also materials which contain suitable replacement atoms for such silicon and/or aluminum. On the other hand, the term "aluminosilicate zeolite" as used herein shall define zeolite materials consisting essentially of silicon and aluminum atoms in the crystalline lattice structure thereof, as opposed to materials which contain substantial amounts of suitable replacement atoms for such silicon and/or aluminum.

Although certain zeolites can be prepared from totally inorganic reaction mixtures, the synthesis of other zeolites is often promoted or made possible by the inclusion of certain organic compounds, termed "organic directing agents", in the reaction mixture. Note the article by Lok et al., "The Role of Organic Molecules in Molecular Sieve Synthesis," Zeolites 3, 282–291 (1983). When such organic directing agents are used, they may be included in an aqueous reaction mixture containing reactants, e.g., sources of silica and alumina, necessary for the zeolite synthesis. The reaction mixture may then be maintained under sufficient conditions, e.g., at elevated temperature, until the desired crystals are formed. These crystals may then be recovered by filtration and washing the filtered crystals with water. This filtering and washing treatment separates the crystals from organic directing agent which is either included in the mother liquor of the reaction mixture or loosely associated with the exterior surface of the crystals. However, a residue of the organic directing agent, e.g., amines and especially quaternary ammonium compounds, usually remains more tenaciously attached to the zeolite crystals. This tenaciously-attached residue, which is not removed by the filtering and washing treatment, may be occluded within the pores of the zeolite and/or firmly affixed to the surface of the zeolite. Certain residues which are tenaciously attached to the zeolite may occupy cation exchange sites of the zeolite, especially in the case of quaternary ammonium residues. It is particularly important to remove organic residue which occludes in the pores of the zeolite because this type of residue may constitute obstructions which tend to substantially reduce the sorption capacity and catalytic activity of the zeolite.

In order to remove the residue of organic directing agents from as-synthesized zeolites, which residue cannot be readily removed by filtration and washing, the zeolite, so long as it is stable under the conditions, may be calcined at elevated temperatures, such as about 400° C. or higher, in the presence of a source of oxygen such as air for at least one hour. This calcination treatment promotes the decomposition and/or volatilization of the residue. The presence of oxygen during the calcination further promotes oxidation, e.g., combustion, of the organic residue into oxidized species, e.g., carbon dioxide, carbon monoxide, water, and nitrogen oxides, which are evolved as gases.

Conventional synthesis of SUZ-9 is taught in European Patent Application 526,252, entirely incorporated herein by reference. The synthesis comprises heating an aqueous reaction mixture under alkaline conditions containing sources of alkali metal oxide, aluminum oxide, silicon oxide, organic directing agent, and water. The organic directing agent is 1,3,4,6,7,9-hexahydro-2,2,5,5,8,8-hexamethyl-2H-benzo (1,2-C:3,5-C':5,6-C") tripyrolium trihydroxide or halide, or its precursor or reaction product, referred to as the tripyrolium compound, and, preferably, tetraethylammonium hydroxide or halide or its precursor or reaction product. The tripyrolium compound is identified in U.S. Pat. No. 3,950,496, incorporated herein by reference, for use as directing agent in synthesis of ZSM-18. The structure of the tripyrolium cation, referred to as "trisquat" in EPA 526,252, may be represented as follows:

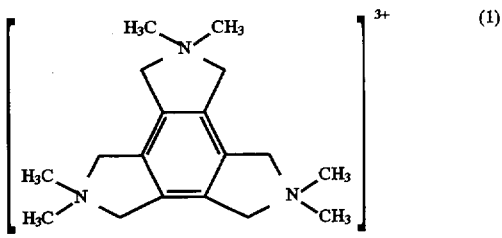

Catalytic cracking is a hydrocarbon conversion process which may utilize certain of the above zeolites as catalyst components. Such a process is commercially employed in the petroleum refining industry to produce useful products, such as high quality gasoline and fuel oils, from hydrocarbon-containing feeds. The endothermic catalytic cracking of hydrocarbons is most commonly practiced in accordance with two known catalytic cracking operations, namely, fluid catalytic cracking (FCC) and moving bed catalytic cracking.

Generally, both fluid catalytic cracking and moving bed operations are commercially practiced in a cyclic mode. During these operations, the hydrocarbon feedstock is contacted with hot, active, solid particulate catalyst without added hydrogen, for example, at pressures of up to about 50 psig and temperatures up to about 650° C. As the hydrocarbon feed is cracked in the presence of cracking catalyst to form more valuable and desirable products, undesirable carbonaceous residue known as "coke" is deposited on the catalyst. The spent catalyst contains coke as well as metals that are present in the feedstock.

Current worldwide refinery trends indicate a continuing need to process heavier feed stock. As a result, many refineries will be processing feedstock containing resids or deeper cut gas oils which have high metals contents. The enhancement of octane produced in catalytic cracking operations is an important goal in the preparation of zeolite containing catalysts. The environmental regulations in the United States and abroad, and the phaseout of lead additives for gasolines in both the U.S. and abroad, provide a strong incentive for refineries to use catalysts which produce increased octane gasolines from heavier metals contaminated feedstock.

U.S. Pat. No. 5,110,776 teaches a method for preparing FCC catalyst comprising modifying the zeolite, e.g., ZSM-5, with phosphorus. U.S. Pat. No. 5,126,298 teaches manufacture of an FCC catalyst comprising zeolite, e.g., ZSM-5, clay, and phosphorus. Phosphorus treatment has been used on faujasite-based cracking catalysts for metals passivation (see U.S. Pat. Nos. 4,970,183 and 4,430,199); reducing coke make (see U.S. Pat. Nos. 4,567,152; 4,584,091; and 5,082,815); increasing activity (see U.S. Pat. Nos. 4,454,241 and 4,498,975); increasing gasoline selectivity (See U.S. Pat. No. 4,970,183); and increasing steam stability (see U.S. Pat. Nos. 4,765,884 and 4,873,211).

In U.S. Pat. No. 3,758,403, use of large-pore cracking catalyst with large amounts of ZSM-5 additive gives only modest increase in light olefin production. A 100% increase in ZSM-5 content (from 5 wt. % ZSM-5 to 10 wt. % ZSM-5) increased the propylene yield less than 20%, and decreased slightly the potential gasoline yield ($C_5$+ gasoline plus alkylate).

U.S. Pat. No. 4,309,280 teaches adding very small amounts of powdered, neat ZSM-5 catalyst, characterized by a particle size below 5 microns. Adding as little as 0.25 wt. % ZSM-5 powder to the FCC catalyst inventory increased LPG production 50%. Small amounts of neat powder behaved much like larger amounts of ZSM-5 disposed in larger particles.

A way to add a modest amount of ZSM-5 to an FCC unit is disclosed in U.S. Pat. No. 4,994,424, incorporated herein by reference. ZSM-5 additive is added to the equilibrium catalyst in a programmed manner so an immediate boost in octane number, typically ½–2 octane number, is achieved.

U.S. Pat. No. 4,927,523, incorporated herein by reference, teaches a way to add large amounts of ZSM-5 to a unit without exceeding wet gas compressor limits. Large amounts are added and cracking severity is reduced in the FCC unit for several days.

It is an object of the present invention to provide an organic compound feedstock conversion process using a new catalyst for manufacture of useful products. For example, use of catalyst comprising improved SUZ-9 will provide octane-enhanced product from a catalytic cracking process, as well as enhanced production of light olefins, e.g., propylene and butylene, in said process.

It is also an object of the present invention to provide a method for selectively separating components in a mixture with a new sorbent composition comprising improved SUZ-9.

SUMMARY OF THE INVENTION

The present invention is directed to use of an improved crystalline material designated SUZ-9 as a sorbent, and for conversion of organic compounds contacted with an active form thereof. The SUZ-9 crystals for use herein are prepared by a novel method comprising forming a reaction mixture hydrogel containing sources of alkali metal (M) cations, e.g., potassium or sodium; an oxide of trivalent element (X), e.g., aluminum, boron, iron, gallium, indium and mixtures thereof; an oxide of tetravalent element (Y), e.g., silicon, germanium, tin and mixtures thereof; an organic directing agent (R), more particularly described as triquat (2) hereinafter; and water, said reaction mixture having a composition in terms of mole ratios, within the following ranges:

| Reactants | Useful | Preferred |
| --- | --- | --- |
| $YO_2/X_2O_3$ | 8 to 30 | 9 to 20 |
| $H_2O/YO_2$ | 8 to 22 | 10 to 18 |
| $OH^-/YO_2$ | 0.4 to 1.1 | 0.5 to 1.0 |
| $M/YO_2$ | 0.2 to 1.3 | 0.4 to 1.9 |
| $R/YO_2$ | 0.03 to 1.2 | 0.04 to 1.0 |

The method further comprises maintaining the reaction mixture until crystals of SUZ-9 structure are formed.

Reaction conditions required consist of heating the foregoing reaction mixture to a temperature of from about 110° C. to about 150° C. for a period of time of from about 40 hours to about 10 days. A more preferred temperature range is from about 130° C. to about 140° C. with the amount of time at a temperature in such range being from about 80 hours to about 5 days.

The solid product comprising SUZ-9 crystals for use in the present invention is recovered from the reaction medium, as by cooling the whole to room temperature, filtering and water washing.

EMBODIMENTS

Figure 1:
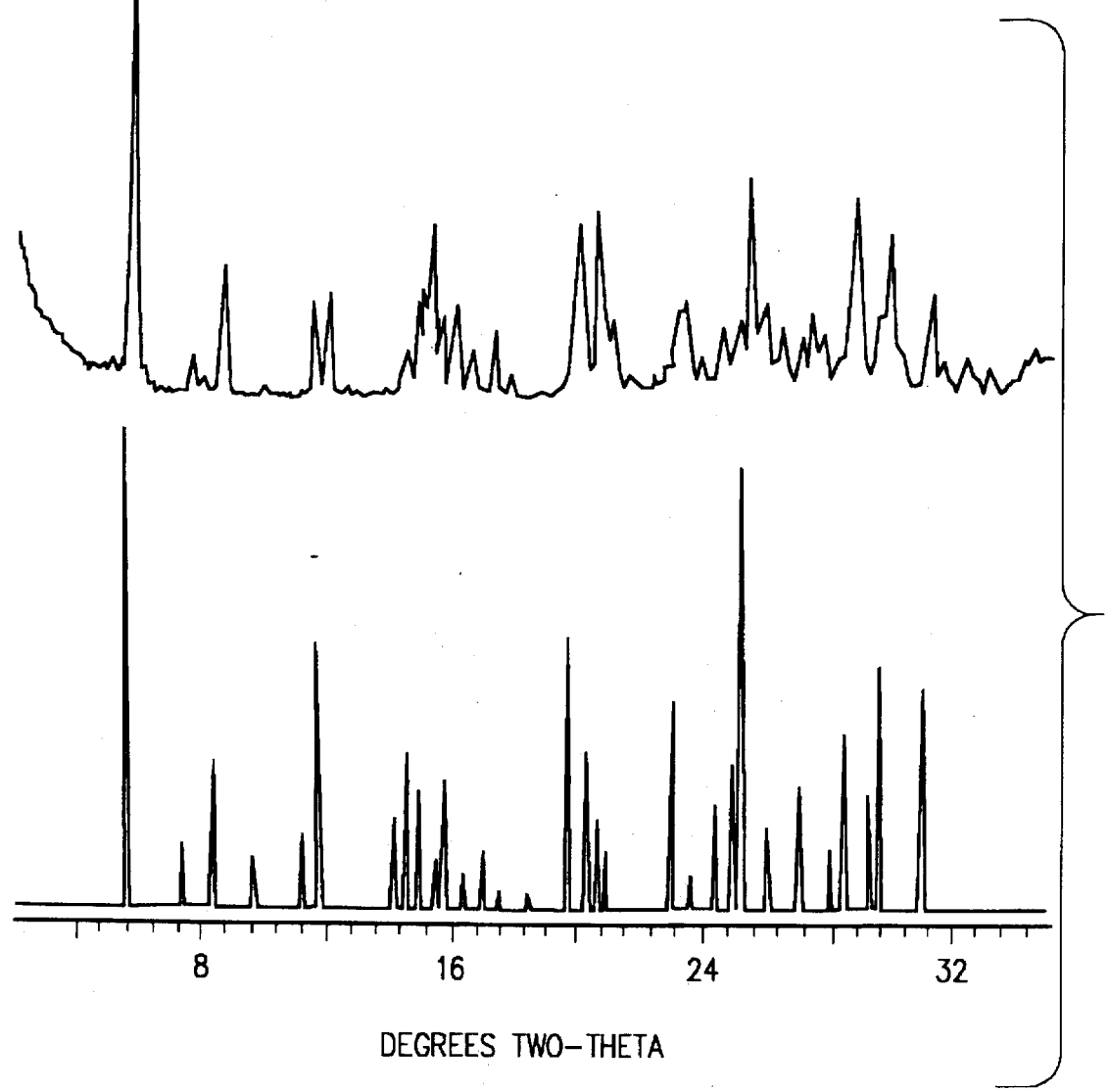
FIG. 1 shows the X-ray pattern for the product of Example 1.

Synthesis of the unique, improved SUZ-9 for use in the present invention requires the different triquat directing agent (R) having a formula $C_{15}H_{39}N_4^{+++}$, which may be represented as follows:

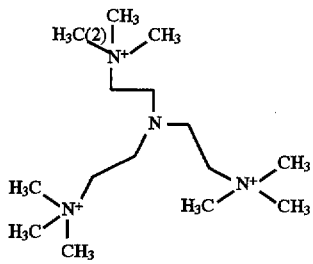

The source of the directing agent may be, for example, the halide, e.g., chloride or bromide, salt. Triquat (2) was synthesized for use herein, as follows:

A 500 mL Parr autoclave was charged with 25 g $(ClCH_2CH_2)3N\cdot HCl$ (Aldrich) and 250 mL MeOH, sealed, cooled in Dry Ice and evacuated to <2 Torr when 50 g $Me_3N$ (anhydrous gas, Aldrich) were run in from an inverted cylinder. The mixture was warmed to room temperature in a water bath, then at 5° C./minute to 92° C., held 7 hours at 92° C., cooled to room temperature, filtered and stripped to give a white paste. The yield of tris-quaternary at this point was 100% with no impurities visible to C-nmr except that the HCl in the original salt had trapped one mole/mole of $Me_3N$ as its hydrochloride. The product was dissolved in 700 mL $H_2O$, eluted over 1 hour through 700 mL IRA-100 anion exchange resin and stripped to about 200 mL on a rotary evaporator. Stripping removed the $Me_3N$. Generally, enough $H_2O$ was stripped to give a 1.15–1.3N (0.38–0.43M in triquat (2)) solution. Titration of the base gave 94–98% yield of a product whose C-nmr showed only the expected peaks at 64.7 (triplet), 55.7 (triplet), and 48.9 vs. DSS in $D_2O$. The product was crystallized from water in low yield as the tetradecahydrate as indicated by elemental analysis and proton nmr.

The particular effectiveness of the presently required organic directing agent, i.e., triquat (2), when compared with any other directing agent, except for the tripyrolium trisquat cation (1) above, for the present synthesis is believed due to its ability to function as a template in the nucleation and growth of SUZ-9 crystals from the above reaction mixture. This is true even though no predigestion of the gel is required prior to crystallization. This different organic agent functions in this fashion in the reaction mixture having the above described composition and under the above described conditions of temperature and time.

It should be noted that the ratio of components of the reaction mixture required herein are critical to achieve maximum effectiveness. For instance, if the $YO_2/X_2O_3$ mole ratio, e.g., $SiO_2/Al_2O_3$ ratio, is too high or the ratio of tetraethylammonium to triquat (2) is too high, something other than SUZ-9 crystal will form. Still further, for most effective synthesis of SUZ-9 by this method, the reaction temperature should be maintained within the range of from about 110° C. to about 150° C., preferably from about 130° C. to about 140° C. The synthesis of SUZ-9 for use in the present invention is facilitated when the reaction mixture comprises seed crystals, such as those having the structure of SUZ-9. The use of at least 0.01%, preferably about 0.10%, and even more preferably about 1% seed crystals (based on total weight) of crystalline material will be useful.

The reaction mixture composition for the synthesis of SUZ-9 crystals for use herein can be prepared utilizing materials which can supply the appropriate oxide. The useful sources of $X_2O_3$, e.g., aluminum oxide, iron oxide and/or boron oxide, include, as non-limiting examples, any known form of such oxide, e.g., aluminum oxide or hydroxide, organic or inorganic salt or compound, e.g., alumina, aluminates and borates. The useful sources of $YO_2$, e.g., silicon oxide, include, as non-limiting examples, known forms of such oxide, e.g., silicic acid or silicon dioxide, alkoxy- or other compounds of silicon, including silica gel and silica hydrosol.

It will be understood that each oxide component utilized in the reaction mixture for the synthesis can be supplied by one or more essential reactants and they can be mixed together in any order. For example, any oxide can be supplied by an aqueous solution. The reaction mixture can be prepared either batchwise or continuously. Crystal size and crystallization time for the product composition comprising the SUZ-9 crystals may vary somewhat with the exact nature of the reaction mixture employed within the above limitations.

The calcined improved SUZ-9 crystal composition prepared hereby has a characteristic X-ray diffraction pattern, including values substantially as set forth in Table I, hereinafter.

TABLE I

| Interplanar d-Spacing, (Å) | Relative Intensity ($I/I_o$) |
|---|---|
| 15.66 ± 0.30 | VS |
| 11.89 ± 0.25 | W |
| 10.46 ± 0.25 | M |
| 9.04 ± 0.15 | VW |
| 7.85 ± 0.15 | M |
| 7.55 ± 0.15 | M/S |
| 6.97 ± 0.15 | VW |
| 6.32 ± 0.12 | W/M |
| 6.13 ± 0.12 | M/S |
| 5.92 ± 0.12 | S |
| 5.80 ± 0.12 | M |
| 5.63 ± 0.12 | M |
| 5.44 ± 0.12 | W/M |
| 5.22 ± 0.12 | M |
| 5.07 ± 0.12 | VW/W |
| 4.48 ± 0.10 | S |
| 4.35 ± 0.10 | S |
| 4.26 ± 0.10 | M/S |
| 3.86 ± 0.08 | M |
| 3.78 ± 0.08 | W/M |
| 3.67 ± 0.08 | W/M |
| 3.60 ± 0.08 | M/S |
| 3.55 ± 0.08 | VS |
| 3.49 ± 0.07 | W/M |
| 3.42 ± 0.07 | W/M |
| 3.35 ± 0.07 | M |
| 3.30 ± 0.07 | M |
| 3.25 ± 0.07 | W/M |
| 3.21 ± 0.07 | W/M |
| 3.14 ± 0.07 | S |
| 3.06 ± 0.07 | M |
| 3.02 ± 0.07 | S |
| 2.89 ± 0.06 | M/S |
| 2.86 ± 0.06 | W |
| 2.78 ± 0.06 | W |
| 2.73 ± 0.06 | VW/W |
| 2.64 ± 0.06 | VW/W |
| 2.59 ± 0.06 | W/M |
| 2.52 ± 0.06 | VW/W |

These X-ray diffraction data were collected with a Scintag theta-theta powder diffraction system, equipped with a graphite diffracted beam monochromator and scintillation counter, using copper K-alpha radiation. The diffraction data were recorded by step-scanning at 0.04 degrees of two-theta, where theta is the Bragg angle, and a counting time of 1 second for each step. The interplanar spacings, d's, were calculated in Angstrom units (A), and the relative intensities of the lines, $I/I_o$, where $I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols VS=very strong (60–100), S=strong (40–60), M=medium (20–40), W=weak (10–20) and VW=very weak (0–10). It should be understood that diffraction data listed for this sample as single lines may consist of multiple overlapping lines which under certain conditions, such as differences in crystallite sizes or very high experimental resolution or crystallographic change, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history.

X-ray diffraction data were also collected on a synchrotron beamline at the National Synchrotron Light Source at Brookhaven, N.Y.

The improved crystalline SUZ-9 prepared for use herein has a composition involving the molar relationship:

$$X_2O_3:(y)\ YO_2$$

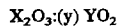

wherein X is a trivalent element, such as aluminum, boron, iron, indium and/or gallium, preferably aluminum; Y is a tetravalent element, such as silicon, tin and/or germanium, preferably silicon; and y is from about 4 to about 8, usually from about 5 to about 7. Any M and R components associated with the as-synthesized material as a result of their presence during crystallization are easily removed by post-crystallization methods hereinafter more particularly described.

Reasons for little having been accomplished with original SUZ-9 include the need, until the present synthesis, for one specific organic directing agent or, preferably, directing agent combination to synthesize it, i.e., tripyrolium trisquat (1) above, or, preferably, trisquat (1) with tetraethylammonium added, and the complexity and cost of tripyrolium trisquat (1) manufacture. Synthesis of tripyrolium trisquat (1) is complex, with low yields, and has a photochemical bromination step if the bromide is desired. See *J. Am. Chem. Soc.*, 100, 2173–2175 (1978).

The improved SUZ-9 synthesized for use herein has distinct advantages over that taught by European Patent Application 526,252, referred to above. First, triquat (2) is easy to manufacture in large quantities. It is available in a one-step synthesis from a fine chemical, i.e., tris (chloroethylamine) hydrochloride, as follows:

$$(ClCH_2CH_2)_3N\cdot HCl + Me_3N \rightarrow (Me_3N^+CH_2CH_2)_3N$$

Tris(choroethylamine) hydrochloride is available from commodity chemicals as follows:

$$N(CH_2CH_2OH)_3 + SOCl_2 \rightarrow (ClCH_2CH_2)_3N\cdot HCl$$

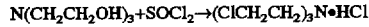

Second, triquat (2) may be easily and routinely removed from the improved SUZ-9 structure without loss of crystallinity or porosity to form the porous, hydrogen form of the zeolite necessary for catalytic applications.

Third, no supplemental organic, e.g., tetraethylammonium hydroxide or halide, is needed for synthesis of pure SUZ-9 by the present invention.

Synthetic improved SUZ-9 prepared as provided herein can be used in the hydrogen form or another univalent or multivalent cationic form. It can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to the SUZ-9 such as, for example, by, in the case of platinum, treating the material with a platinum metal-containing ion. Suitable platinum compounds for this purpose include chloroplatinic acid, platinum chloride and various compounds containing the platinum amine complex. Combinations of metals and methods for their introduction can also be used.

Synthetic improved SUZ-9 crystals, when employed either as an adsorbent or as a catalyst in a hydrocarbon conversion process, should be dehydrated at least partially. This can be done by heating to a temperature in the range of from about 65° C. to about 315° C. in an inert atmosphere, such as air, nitrogen, etc., and at atmospheric or subatmospheric pressures for between 1 and 48 hours. Dehydration can be performed at lower temperature merely by placing the zeolite in a vacuum, but a longer time is required to obtain a particular degree of dehydration. The crystalline thermal decomposition product of the newly synthesized SUZ-9 can be prepared by heating same at a temperature of from about 200° C. to about 550° C. for from 1 hour to about 48 hours.

The original cations, e.g., alkali metal, of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which render the material catalytically active, especially for certain hydrocarbon conversion reactions. These include hydrogen, rare earth metals and metals of Groups IIA, IIIA, IVA, IB, IIB, IIIB, IVB, and VIII of the Periodic Table of the Elements, especially gallium, indium, and tin.

Typical ion exchange technique would be to contact the synthetic SUZ-9 material with a salt of the desired replacing cation or cations. Examples of such salts include the halides, e.g., chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the improved SUZ-9 for use herein is then preferably washed with water and dried at a temperature ranging from 65° C. to about 315° C. and thereafter may be calcined in air or other inert gas at temperatures ranging from about 200° C. to about 550° C. for periods of time ranging from 1 to 48 hours or more to produce a catalytically-active crystalline thermal decomposition product thereof.

The improved crystalline SUZ-9 for use herein may be formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the crystalline material can be extruded before drying or dried or partially dried and then extruded.

The SUZ-9 prepared as above may be used as an adsorbent, such as for separating at least one component from a mixture of components in the vapor or liquid phase having differential sorption characteristics with respect to the improved SUZ-9. Therefore, at least one component can be partially or substantially totally separated from a mixture of components having differential sorption characteristics with respect to SUZ-9 by contacting the mixture with the SUZ-9 to selectively sorb the one component.

The SUZ-9 prepared as herein provided can be used to catalyze a wide variety of chemical conversion processes including many of present commercial/industrial importance. Conversion conditions, in general, include a temperature of from about −25° C. to about 650° C., a pressure of from about atmospheric to about 5,000 psig, and a weight hourly space velocity of from about 0.01 to about 2,000 hr$^{-1}$. Conversion conditions, in general, for cracking include a temperature of from about 400° C. to about 650° C. and a pressure of from about atmospheric to about 5 atmospheres. Examples of chemical conversion processes which are effectively catalyzed by improved SUZ-9, by itself or in combination with one or more other catalytically active substances including other crystalline catalysts, include those requiring a catalyst with acid activity. Specific examples include:

(1) alkylation of aromatic hydrocarbons, e.g., benzene, with long chain olefins of six or more carbon atoms, e.g., $C_6$–$C_{14}$ olefin, with reaction conditions including a temperature of from about 340° C. to about 500° C., a pressure of from about atmospheric to about 200 atmospheres, a weight hourly space velocity of from about 2 hr$^{-1}$ to about 2000 hr$^{-1}$ and an aromatic hydrocarbon/olefin mole ratio of from about 1/1 to about 20/1, to provide long chain alkyl aromatics which can be subsequently sulfonated to provide synthetic detergents;

(2) alkylation of aromatic hydrocarbons with gaseous olefins to provide short chain alkyl (e.g., $C_2$–$C_5$) aromatic compounds, e.g., the alkylation of benzene with propylene to provide cumene, with reaction conditions including a temperature of from about 10° C. to about 125° C., a pressure of from about 1 to about 30 atmospheres, and an aromatic hydrocarbon weight hourly space velocity (WHSV) of from 5 hr$^{-1}$ to about 50 hr$^{-1}$;

(3) alkylation of reformate containing substantial quantities of benzene and toluene with fuel gas containing $C_5$ olefins to provide, inter alia, mono- and dialkylates with reaction conditions including a temperature of from about 315° C. to about 455° C., a pressure of from about 400 to about 800 psig, a WHSV-olefin of from about 0.4 hr$^{-1}$ to about 0.8 hr$^{-1}$, a WHSV-reformate of from about 1 hr$^{-1}$ to about 2 hr$^{-1}$ and a gas recycle of from about 1.5 to 2.5 vol/vol fuel gas feed;

(4) alkylation of aromatic hydrocarbons, e.g., benzene, toluene, xylene and naphthalene, with long chain olefins of six or more carbon atoms, e.g., $C_6$–$C_{14}$ olefin, to provide alkylated aromatic lube base stocks with reaction conditions including a temperature of from about 160° C. to about 260° C. and a pressure of from about 350 to 450 psig;

(5) alkylation of phenols with an alkylation agent selected from the group consisting of long chain, e.g., $C_6$–$C_{14}$, olefins or equivalent alcohols to provide long chain alkyl phenols with reaction conditions including a temperature of from about 200° C. to about 250° C., a pressure of from about 200 to 300 psig and a total WHSV of from about 2 hr$^{-1}$ to about 10 hr$^{-1}$; and (6) alkylation of isoalkanes, e.g., isobutane, with olefins, e.g., 2-butene, with reaction conditions including a temperature of from about −25° C. to about 400° C., e.g., from 75° C. to 200° C., a pressure of from below atmospheric to about 35000 kPa (5000 psig), e.g., from 100 to 7000 kPa (1 to 1000 psig), a weight hourly space velocity based on olefin of from about 0.01 hr$^{-1}$ to about 100 hr$^{-1}$, e.g., from 0.1 hr$^{-1}$ to 20 hr$^{-1}$, and a mole ratio of total isoalkane to total olefin of from about 1:2 to about 100:1, e.g., from 3:1 to 30:1.

In catalytic cracking over catalyst comprising improved SUZ-9, high molecular weight hydrocarbons are converted to lower molecular weight hydrocarbons of suitable volatility to permit their use as liquid fuels. The combustion characteristics of gasoline are assessed empirically by assigning the fuel an octane rating. This is generally defined as a comparison with a primary reference which is the percentage of iso-octane (2,2,4-trimethylpentane) in an n-heptane/iso-octane mixture to which the gasoline under examination is equivalent in terms of combustion behavior when considering the octane ratings of n-heptane and iso-octane to be zero and 100 respectively. Both RON and MON can be tested on the same single-cylinder, four-stroke engine of standardized design. RON signifies the research octane number, MON signifies the motor octane number, and the terms are used to describe the knocking characteristics of gasoline, that is, its combustion behavior. For a measurement of RON, the engine speed used is 600 rpm which yields results comparable to an automobile engine operated at low speed. For a measurement of MON, the engine speed is 900 rpm which approximates higher speed cruising conditions. Generally, higher octane numbers are found by the research method compared to the motor method for the same gasoline sample. The average of the RON and MON, known as the road octane number, gives an indication of typical performance in an engine. The higher the octane, the better the combustion behavior in a spark-ignition engine. It has been found that road octane number correlates much more closely to the motor octane number than the research octane. Generally, aromatics and branched paraffinic and olefinic hydrocarbons have higher octane values than acyclic or linear paraffinic hydrocarbons.

In conjunction with catalytic cracking to produce gasoline product, alkylate and potential alkylate may result from the cracking process. This indirectly leads to product of increased octane because high octane, highly branched paraffinic gasoline blending stocks are produced principally by alkylation of $C_3$ and $C_4$ olefins with isobutane. Unlike cracking, alkylation makes larger branched hydrocarbons from smaller hydrocarbons and these larger branched hydrocarbons are inherently higher in octane.

The present process provides not only a high octane product, but significantly more light olefins, especially propylene and butylene. The lower olefins of this product are high quality, petrochemical grade, and may be used for manufacture of valuable ethers and/or alcohols, or as alkylating agents.

The feedstock for a cracking process using improved SUZ-9 catalyst, that is, the hydrocarbons to be cracked, may include in whole or in part, a gas oil (e.g., light, medium, or heavy gas oil) having an initial boiling point above about 204° C., a 50% point of at least about 260° C., and an end point of at least about 315° C. The feedstock may also include deep cut gas oil, vacuum gas oil, thermal oil, residual oil, cycle stock, whole top crude, tar sand oil, shale oil, synthetic fuel, heavy hydrocarbon fractions derived from the destructive hydrogenation of coal, tar, pitches, asphalts, hydrotreated feedstocks derived from any of the foregoing, and the like. As will be recognized, the distillation of higher boiling petroleum fractions above about 400° C. must be carried out under vacuum in order to avoid thermal cracking. The boiling temperatures utilized herein are expressed in terms of convenience of the boiling point corrected to atmospheric pressure. Resids or deeper cut gas oils having an end point of up to about 700° C., even with high metals contents, can also be cracked using the invention.

The present invention provides a process for converting feedstock hydrocarbon compounds to product hydrocarbon compounds of lower molecular weight than the feedstock hydrocarbon compounds. In particular, the present invention provides a process for catalytically cracking a hydrocarbon feed to a mixture of products comprising gasoline, alkylate, potential alkylate, and lower olefins, e.g., propylene, in the presence of a cracking catalyst under catalytic cracking conditions. Catalytic cracking units which are amenable to the process of the invention operate at temperatures from about 400° C. to about 650° C., usually from about 450° C. to about 600° C., and under reduced, atmospheric, or superatmospheric pressure, usually from about atmospheric to about 5 atmospheres. The catalytic process can be either fixed bed, moving bed, transfer line, or fluidized bed, and the hydrocarbon flow may be either concurrent or countercurrent to the catalyst flow. The process of the invention is particularly applicable to the Fluid Catalytic Cracking (FCC) or Thermofor Catalytic Cracking (TCC) processes. In both of these processes, the hydrocarbon feed and catalyst are passed through a reactor and the catalyst is regenerated. The two processes differ substantially in the size of the catalyst particles and in the engineering contact and transfer which is at least partially a function of catalyst size.

The TCC process is a moving bed and the catalyst is in the shape of pellets or beads having an average particle size of about one-sixty-fourth to one-fourth inch. Active, hot catalyst beads progress downwardly cocurrent with a hydrocarbon charge stock through a cracking reaction zone. The hydrocarbon products are separated from the coked catalyst and recovered, and the catalyst is recovered at the lower end of the zone and regenerated.

Typically preferred TCC conversion conditions include an average reactor temperature of from about 450° C. to about 540° C.; catalyst/oil volume ratio of from about 2 to about 7; reactor volume hourly space velocity of from about 1 to about 5 vol./hr./vol.; and recycle to fresh feed ratio of from 0 to about 0.5 (volume).

The process of the invention is particularly applicable to Fluid Catalytic Cracking. In fluidized catalytic cracking processes, the catalyst is a fine powder of about 10 to 200 microns. This powder is generally suspended in the feed and propelled upward in a reaction zone. A relatively heavy hydrocarbon feedstock, e.g., a gas oil, is admixed with a suitable cracking catalyst to provide a fluidized suspension and cracked in an elongated reactor, or riser, at elevated temperatures to provide a mixture of lighter hydrocarbon products. The gaseous reaction products and spent catalyst are discharged from the riser into a separator, e.g., a cyclone unit, located within the upper section of an enclosed stripping vessel, or stripper, with the reaction products being conveyed to a product recovery zone and the spent catalyst entering a dense catalyst bed within the lower section of the stripper. In order to remove entrained hydrocarbons from the spent catalyst prior to conveying the latter to a catalyst regenerator unit, an inert stripping gas, e.g., steam, is passed through the catalyst bed where it desorbs such hydrocarbons conveying them to the product recovery zone. The fluidizable catalyst is continuously circulated between the riser and the regenerator and serves to transfer heat from the latter to the former thereby supplying the thermal needs of the cracking reaction which is endothermic.

Gas from the FCC main-column overhead receiver is compressed and directed with primary-absorber bottoms and stripper overhead gas through a cooler to the high pressure receiver. Gas from this receiver is routed to the primary absorber, where it is contacted by the unstabilized gasoline from the main-column overhead receiver. The net effect of this contacting is a separation between $C_3+$ and $C_2-$ fractions in the feed to the primary absorber. Primary absorber off-gas is directed to a secondary or sponge absorber, where a circulating stream of light cycle oil from the main column is used to absorb most of the remaining $C_5+$ material in the sponge absorber feed. Some $C_3$ and $C_4$ materials are also absorbed. The sponge-absorber rich oil is returned to the FCC main column. The sponge-absorber overhead, with most of the valuable $C_4+$ material removed but including $H_2S$, is sent to the fuel gas or other process streams.

Liquid from the high pressure separator is sent to a stripper where most of the $C_2-$ is removed overhead and sent back to the high pressure separator. The bottoms liquid from the stripper is sent to the debutanizer, where an olefinic $C_3-C_4$ product is further separated for gasoline production. The debutanizer bottoms, that is, the stabilized gasoline, is sent to treating, if necessary, and then to storage. The $C_3$ and $C_4$ product olefins can be directed to an alkylation unit to produce a high octane gasoline by the reaction of an iso-paraffin (usually iso-butane) with one or more of the low molecular weight olefins (usually propylene and butylene).

The FCC conversion conditions include a riser top temperature of from about 500° C. to about 595° C., preferably from about 520° C. to about 565° C., and most preferably from about 530° C. to about 550° C.; catalyst/oil weight ratio of from about 3 to about 12, preferably from about 4 to about 11, and most preferably from about 5 to about 10; and catalyst residence time of from about 0.5 to about 15 seconds, preferably from about 1 to about 10 seconds.

In the FCC process, the improved SUZ-9 component may be combined with a large-pore molecular sieve component which may comprise any active component having cracking activity and which has a pore opening of greater than about 7 Angstroms in effective diameter. The active component may be a conventional large-pore molecular sieve including zeolite X (U.S. Pat. No. 2,882,442); REX; zeolite Y (U.S. Pat. No. 3,130,007); Ultrastable Y (USY) (U.S. Pat. No. 3,449,070); Rare Earth exchanged Y (REY) (U.S. Pat. No. 4,415,438); Rare Earth exchanged USY (REUSY); Dealuminated Y (DeAl Y) (U.S. Pat. Nos. 3,442,792 and 4,331,694); Ultrahydrophobic Y (UHPY) (U.S. Pat. No. 4,401,556); and/or dealuminated silicon-enriched zeolites, e.g., LZ-210 (U.S. Pat. No. 4,678,765). Preferred are higher silica forms of zeolite Y. ZSM-20 (U.S. Pat. No. 3,972,983); zeolite Beta (U.S. Pat. No. 3,308,069); zeolite L (U.S. Pat. Nos. 3,216,789 and 4,701,315); and naturally occurring zeolites such as faujasite, mordenite and the like may also be used. These materials may be subjected to conventional treatments, such as impregnation or ion exchange with rare earths to increase stability. These patents are incorporated herein by reference. In current commercial practice most cracking catalysts contain these large-pore molecular sieves. The preferred molecular sieve of those listed above is a zeolite Y, more preferably an REY, USY or REUSY.

Other large-pore crystalline molecular sieves include pillared silicates and/or clays; aluminophosphates, e.g., ALPO$_4$-5, ALPO$_4$-8, VPI-5; silicoaluminophosphates, e.g., SAPO-5, SAPO-37, SAPO-40, MCM-9; and other metal aluminophosphates. Mesoporous crystalline material for use as the molecular sieve includes MCM-41. These are variously described in U.S. Pat. Nos. 4,310,440; 4,440,871; 4,554,143; 4,567,029; 4,666,875; 4,742,033; 4,880,611; 4,859,314; 4,791,083; 5,102,643; and 5,098,684, each incorporated herein by reference.

The SUZ-9 and/or large-pore molecular sieve catalyst component may include phosphorus or a phosphorus compound for any of the functions generally attributed thereto, such as, for example, attrition resistance, stability, metals passivation, and coke make reduction.

To prepare the large-pore molecular sieve component for use herein, a slurry may be formed by deagglomerating the molecular sieve, preferably in an aqueous solution. A slurry of the matrix material may be formed by mixing the desired matrix components such as clay and/or inorganic oxide in an aqueous solution. The molecular sieve slurry and the matrix slurry are then well mixed and spray dried to form catalyst particles of, for example, less than 200 microns in diameter.

It is conventional to use an additive catalyst with different properties along with a conventional catalyst to form an optional mixed catalyst system. We now offer that improved SUZ-9 may be used as an additive catalyst for this purpose. Commercially used additives are shape-selective zeolites. Zeolites having a Constraint Index of 1–12 have been used for this purpose. Details of the Constraint Index test are provided in *J.Catalysis*, 67, 218–222 (1981) and in U.S. Pat. No. 4,711,710 both of which are incorporated herein by reference.

Conventional shape-selective zeolites useful for this purpose are exemplified by large pore (e.g., greater than about 7 Angstroms pore size) zeolite Beta (U.S. Pat. No. 3,308,069); intermediate pore (e.g., pore size of from about 4 to about 7 Angstroms) zeolites ZSM-5 (U.S. Pat. No. 3,702,886 and U.S. Pat. No. Re. 29,948); ZSM-11 (U.S. Pat. No. 3,709,979); ZSM-12 (U.S. Pat. No. 4,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); PSH-3 (U.S. Pat. No. 4,439,409); and MCM-22 (U.S. Pat. No. 4,954,325); and small pore (e.g., having pore openings of less than about 4 Angstroms diameter) zeolites ZSM-34 and erionite, either alone or in combination. In addition, the catalyst composition may include metals useful in promoting the oxidation of carbon monoxide to carbon dioxide under regenerator conditions as described in U.S. Pat. No. 4,350,614. The additive catalyst may also include phosphorus or a phosphorus compound for any of the functions generally attributed thereto.

The large-pore molecular sieve component of catalyst for use herein may comprise from about 5 to about 60 weight percent of the catalyst composition. The additive catalyst component, i.e., improved SUZ-9 catalyst, may comprise from about 0.5 to about 50, for example, from about 2 to about 50, weight percent of the catalyst composition. For the additive catalyst, the SUZ-9 may comprise from at least about 25 to less than about 60 weight percent of the additive catalyst component composition.

Although neither the cracking catalyst nor the additive catalyst need be steamed prior to use in the present process, they may be steamed at a temperature of from about 300° C. to about 800° C. for a time of from about 1 to about 200 hours in about 5 to about 100% steam.

In an embodiment of the present invention, the catalyst composition may include metals useful in promoting the oxidation of carbon monoxide to carbon dioxide under catalyst regeneration conditions as described in U.S. Pat. Nos. 4,072,600 and 4,350,614, the entire contents of each incorporated herein by reference. Examples of this embodiment include addition to the catalyst composition for use herein trace amounts of oxidation promoter selected from the group consisting of platinum, palladium, iridium, osmium, rhodium, ruthenium, rhenium, and combination thereof. The catalyst composition may comprise, for example, from about 0.01 ppm to about 100 ppm by weight oxidation promoter, usually from about 0.01 ppm to about 50 ppm by weight, preferably from about 0.01 ppm to about 5 ppm by weight.

Employing a catalytically active form of the improved SUZ-9 catalyst which may contain additional hydrogenation components, reforming stocks can be reformed employing a temperature between about 370° C. and about 540° C. The pressure can be between about 100 psig and about 1000 psig, but it is preferably between about 200 psig and about 700 psig. The liquid hourly space velocity is generally between about 0.1 and about 10 hr$^{-1}$, preferably between about 0.5 and about 4 hr$^{-1}$, and the hydrogen to hydrocarbon mole ratio is generally between about 1 and about 20, preferably between about 4 and about 12.

The improved SUZ-9 catalyst can also be used for hydroisomerization of normal paraffins, when provided with a hydrogenation component, e.g., platinum. Hydroisomerization is carried out at a temperature between about 90° C. and 375° C., preferably about 145° C. to about 290° C., with a liquid hourly space velocity between about 0.01 and about 2 hr$^{-1}$, preferably between about 0.25 and about 0.50 hr$^{-1}$, employing hydrogen such that the hydrogen to hydrocarbon mole ratio is between about 1:1 and about 5:1.

The catalyst can also be used for reducing the pour point of gas oils. This reaction may be conducted at a liquid hourly space velocity between about 10 and about 30 hr$^{-1}$ and at a temperature between about 400° C. and about 540° C.

Other reactions which can be accomplished employing the SUZ-9 catalyst of this invention containing a metal, e.g., platinum, include hydrogenation-dehydrogenation reactions and desulfurization reactions. The new and improved SUZ-9 of the present invention will perform as an improved sorbent or catalyst for all the processes disclosed for original SUZ-9 use in European Patent Application 526,252.

In the case of many catalysts, it is desired to incorporate the improved SUZ-9 with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the SUZ-9, i.e., combined therewith or present during synthesis of SUZ-9, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present SUZ-9 layered material also include inorganic oxides, notably alumina.

In addition to the foregoing materials, the SUZ-9 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. 5 The relative proportions of finely divided improved SUZ-9 material and inorganic oxide matrix vary widely, with the SUZ-9 content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078; in the *Journal of Catalysis*, vol. 4, 527 (1965); vol. 6, 278 (1966); and vol. 61, 395 (1980), each incorporated herein by reference as to that description. The experimental conditions of the test used herein include a constant temperature of 538° C. and a variable flow rate as described in detail in the *Journal of Catalysis*, vol. 61, 395.

EXAMPLE 1

This preparation was essentially identical to Example 5 of EPA 526,252 except that triquat ion (2) was substituted for the tripyrolium trisquat (1). To a solution of 4.11 g KOH and 15.8 mL 1.83N triquat (2) hydroxide prepared above were added 9.5 g Cabosil fumed silica. Simultaneously 2.6 g sodium aluminate were dissolved in 20.2 mL H$_2$O. When the sodium aluminate has all dissolved, the two solutions were mixed, stirred magnetically for 3 hours at room temperature, sealed in a stainless steel reactor, and heated for 93 hours at 135° C. without stirring. The product was centrifuged, washed twice with 100 mL H$_2$O, and dried overnight at 85° C. to give 6.7 g product.

The product was calcined by heating 3° C./minute to 500° C. under flowing N$_2$, holding for 3 hours at 500° C., cooling to 250° C., heating 3° C./minute to 500° C. under flowing air, holding for 6 hours at 500° C., and cooling under N$_2$. This product was exchanged 3 times with 20 mL/g 1M NH$_4$Cl (pH adjusted to 8.0 with NH$_4$OH) and recalcined 3° C./minute to 500° C. under flowing air and holding for 3 hours at 500° C. before cooling.

The product calcined SUZ-9 was analyzed by X-ray diffraction and found to exhibit the pattern shown in FIG. 1.

In FIG. 1, the actual Scintag X-ray data for the product of this example is presented at the top of the Figure. A simulation of peak positions and intensities from the values of Table I is presented at the bottom of FIG. 1 for comparison.

EXAMPLE 2

This preparation was essentially identical to Example 2 of EPA 526,252 except that triquat ion (2) was substituted for tripyrolium trisquat (1) and a vertical stirring shaft was used instead of revolving the pressure vessel. To a solution of 5.71 g KOH, 14.4 mL 1.83N triquat (2) hydroxide, and 34.9 g 25% tetraethylammonium hydroxide were added 14.2 g Cabosil fumed silica. Simultaneously 3 0 g sodium aluminate were dissolved in 20 mL H$_2$O. The solutions were mixed and stirred magnetically, then sealed in a 300 mL Barr reactor with 3 blades set to sweep the entire depth of the solution. The mixture was stirred 8–10 rpm, heated 2° C./minute to 135° C., and held at that temperature for 116 hours. The recovered solid product was calcined, NH$_4$Cl exchanged, and recalcined as described in Example 1.

The product calcined SUZ-9 was analyzed by X-ray diffraction on the synchrotron beamline and found to be essentially pure SUZ-9 exhibiting the X-ray data of Table II.

TABLE II

| Interplanar d-spacing (A) | Relative Intensity |
|---|---|
| 32.23 | VW |
| 18.10 | VW |
| 15.68 | VS |
| 11.84 | W |
| 11.35 | W |
| 10.44 | M |
| 9.04 | VW |
| 7.84 | VW |
| 7.81 | VW |
| 7.54 | W |
| 6.96 | VW |
| 6.35 | VW |
| 6.26 | VW |
| 6.11 | W |
| 6.02 | W |
| 5.91 | M |
| 5.79 | VW |
| 5.62 | W |
| 5.43 | W |
| 5.21 | VW |
| 5.20 | VW |
| 5.06 | VW |
| 4.52 | VW |
| 4.51 | VW |
| 4.47 | M |
| 4.34 | M |
| 4.29 | VW |
| 4.25 | W |
| 3.87 | VW |
| 3.84 | W |
| 3.66 | VW |
| 3.59 | W |
| 3.55 | M |
| 3.50 | VW |
| 3.41 | W |
| 3.34 | W |
| 3.30 | W |
| 3.25 | VW |
| 3.19 | VW |
| 3.13 | M |
| 3.06 | VW |
| 3.01 | M |

EXAMPLE 3

The product of Example 2 was evaluated for sorption of n-hexane at 40 Torr and 25° C. to compare with the sorption result reported for the Example 2 product of EPA 526,252. The presently prepared SUZ-9 had an n-hexane sorption capacity of 10.6%, compared to the reported n-hexane sorption capacity of the prior art preparation of SUZ-9 of 6.8% at 80 Torr and 25° C. The sorption of n-hexane by SUZ-9 made by the present invention is thus at least 50% greater than that claimed in EPA 526,252, and will always be greater than about 9% for n-hexane at 40 Torr and 25° C. Note that sorption increases with pressure and the maximum pressure used herein was less than that in the reference. The higher sorption may indicate either that use of the presently required template, i.e., triquat (2), makes a purer product, or that less crystallinity loss occurs during calcination, or both.

EXAMPLE 4

A sample of the product of Example 2 was subjected to the Alpha Test and found to have an Alpha Value of 43. This value aged to 35 after 1 hour at 530° C. under standard conditions.

Changes and modifications in the specifically described embodiments can be carried out without departing from the scope of the invention which is intended to be limited only by the scope of the appended claims.

What is claimed is:

1. A process for convening a feedstock comprising organic compounds to conversion product, which process is selected from the group consisting of aromatics alkylation, alkylation of isoalkanes, catalytic cracking and reforming and which comprises contacting said feedstock at organic compound conversion conditions with a catalyst composition comprising an active form of crystalline material exhibiting a characteristic X-ray diffraction pattern including d-spacing maxima values as shown in Table I, said crystalline material having been synthesized by a method comprising (i) preparing a mixture capable, to forming said material, said mixture comprising sources of alkali metal (M), an oxide of trivalent element (X), an oxide of tetravalent element (Y), water and triquat (R) having a formula $C_{15}H_{39}N_4^{+++}$ and represented as follows:

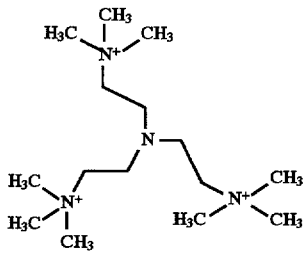

and having a composition, in terms of mole ratios, within the following ranges:

| | |
|---|---|
| $YO_2/X_2O_3$ | 8 to 30 |
| $H_2O/YO_2$ | 8 to 22 |
| $OH^-/YO_2$ | 0.4 to 1.1 |
| $M/YO_2$ | 0.2 to 1.3 |
| $R/YO_2$ | 0.03 to 1.2; |

(ii) maintaining said mixture under sufficient conditions including a temperature of from about 110° C. to about 150° C. until crystals of said material are formed; and (iii) recovering said crystalline material from step (ii), said recovered crystalline material containing said R.

2. The process of claim 1 wherein said mixture has the following composition ranges:

| | |
|---|---|
| $YO_2/X_2O_3$ | 9 to 20 |
| $H_2O/YO_2$ | 10 to 18 |
| $OH^-/YO_2$ | 0.5 to 1.0 |
| $M/YO_2$ | 0.4 to 1.0 |
| $R/YO_2$ | 0.04 to 1.0. |

3. The process of claim 1 wherein said X is aluminum, boron, iron, gallium, indium or a mixture thereof, and said Y is silicon, germanium, tin or a mixture thereof.

4. The process of claim 1 wherein X comprises aluminum and Y comprises silicon.

5. The process of claim 1 wherein said crystalline material synthesis method comprises replacing ions of the crystalline material recovered in step (iii), at least in part, by ion exchange with an ion or a mixture of ions selected from the group consisting of hydrogen and hydrogen precursors, rare earth metals and metals from Groups IIA, IIIA, IVA, IB, IIB, IIIB, IVB, VIB and VIII of the Periodic Table of Elements.

6. The process of claim 2 wherein said crystalline material synthesis method comprises replacing ions of the crystalline material recovered in step (iii), at least in part, by ion exchange with an ion or a mixture of ions selected from the group consisting of hydrogen and hydrogen precursors, rare earth metals and metals from Groups IIA, IIIA, IVA, IB, IIB, IIIB, IVB, VIB and VIII of the Periodic Table of Elements.

7. The process of claim 5 wherein said replacing ion is hydrogen or a hydrogen precursor.

8. The process of claim 6 wherein said replacing ion is hydrogen or a hydrogen precursor.

9. The process of claim 1 wherein said catalyst composition further comprises a matrix selected from the group consisting of alumina, silica, zirconia, titania, magnesia, beryllia, and a combination thereof.

10. The process of claim 1 wherein said conversion conditions include a temperature of from about −25° C. to about 650° C. and a pressure of from about atmospheric to about 5,000 psig.

11. The process of claim 1 wherein said process is aromatics alkylation and wherein said feedstock comprises aromatic compounds and olefins of six or more carbon atoms, and said conversion conditions include a temperature of from about 340° C. to about 500° C., a pressure of from about atmospheric to about 200 atmospheres, a weight hourly space velocity of from about 2 $hr^{-1}$ to about 2000 $hr^{-1}$, and an aromatic compound/olefin mole ratio of from about 1/1 to about 20/1.

12. The process of claim 1 wherein said process is aromatics alkylation and wherein said feedstock comprises aromatic compounds and olefins of two to five carbon atoms, and said conversion conditions including a temperature of from about 10° C. to about 125° C., a pressure of from about 1 to about 30 atmospheres, and an aromatic hydrocarbon weight hourly space velocity of from about 5 $hr^{-1}$ to about 50 $hr^{-1}$.

13. The process of claim 1 wherein said process is aromatics alkylation and wherein said feedstock comprises reformate and fuel gas, and said conversion conditions include a temperature of from about 315° C. to about 455° C. and a pressure of from about 400 psig to about 800 psig.

14. The process of claim 1 wherein said process is aromatics alkylation and wherein said feedstock comprises aromatic compounds selected from the group consisting of benzene, toluene, xylene, and naphthalene, and olefins of six or more carbon atoms, and said conversion conditions include a temperature of from about 160 ° C. to about 260 ° C. and a pressure of from about 350 psig to about 450 psig.

15. The process of claim 1 wherein said process is aromatics alkylation and wherein said feedstock comprises phenols and an alcohol or olefin having 6 to 14 carbon atoms, and said conversion conditions include a temperature of from about 200° C. to about 250° C., a pressure of from about 200 psig to about 300 psig, and a weight hourly space velocity of from about 2 hr$^{-1}$ to about 10 hr$^{-1}$.

16. The process of claim 1 wherein said process is alkylation of isoalkanes and wherein said feedstock comprises isoalkanes and olefins, and said conversion conditions include a temperature of from about −25° C. to about 400° C., a pressure of from below atmospheric to about 5000 psig, a weight hourly space velocity of from about 0.01 hr$^{-1}$ to about 100 hr$^{-1}$, and a mole ratio of total isoalkanes/total olefins of from about ½ to about 100/1.

17. The process of claim 16 wherein said isoalkanes comprise isobutane and said olefins comprise 2-butene.

18. A process for converting feedstock hydrocarbon compounds to product hydrocarbon compounds having a lower molecular weight than the feedstock hydrocarbon compounds which comprises contacting said feedstock at conversion conditions with a catalyst composition comprising an active form of crystalline material exhibiting a characteristic X-ray diffraction pattern including d-spacing maxima values as shown in Table I, said crystalline material having been synthesized by a method comprising (i) preparing a mixture capable of forming said material, said mixture comprising sources of alkali metal (M), an oxide of trivalent element (X), an oxide of tetravalent element (Y), water and triquat specification (R) having a formula $C_{13}H_{39}N_4^{+++}$ and represented as follows:

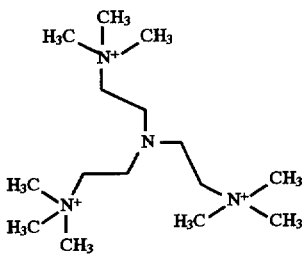

and having a composition, in terms of mole ratios, within the following ranges:

| | |
|---|---|
| YO$_2$/X$_2$O$_3$ | 8 to 30 |
| H$_2$O/YO$_2$ | 8 to 22 |
| OH$^-$/YO$_2$ | 0.4 to 1.1 |
| M/YO$_2$ | 0.2 to 1.3 |
| R/YO$_2$ | 0.03 to 1.2; |

(ii) maintaining said mixture under sufficient conditions including a temperature of from about 110° C. to about 150° C. until crystals of said material are formed; and (iii) recovering said crystalline material from step (ii), said recovered crystalline material containing said R.

19. The process of claim 18 wherein said catalyst composition further comprises a matrix selected from the group consisting of alumina, silica, zirconia, titania, magnesia, beryllia, and a combination thereof.

20. The process of claim 18 wherein said conversion conditions include temperature of from about 400° C. to about 650° C. and a pressure of from atmospheric to about 5 atmospheres.

21. The process of claim 18 wherein said conversion conditions include an average reactor temperature of from about 450° C. to about 540° C., a catalyst/oil volume ratio of from about 2 to about 7, and a space volume hourly velocity of from about 1 to about 5 hr$^{-1}$.

22. The process of claim 18 wherein said conversion conditions include a riser top temperature of from about 500° C. to about 595° C., a catalyst/oil volume ratio of from about 3 to about 12, and a catalyst residence time of from about 0.5 to about 15 seconds.

23. The process of claim 18 wherein said catalyst composition further comprises a molecular sieve material having pore openings of greater than about 7 Angstroms, said molecular sieve material being selected from the group consisting of zeolites REY, USY, REUSY, dealuminated Y, ultrahydrophobic Y, silicon-enriched dealuminated Y, ZSM-20, Beta, L, silicoalumino-phosphates SAPO-5, SAPO-37, SAPO-40, MCM-9, metallo-aluminophosphate MAPO-36, aluminophosphate VPI-5, and mesoporous crystalline MCM-41.

24. The process of claim 23 wherein the molecular sieve material comprises REY, USY, or REUSY.

25. The process of claim 23 wherein said catalyst composition further comprises phosphorus.

26. The process of claim 18 wherein said feedstock comprises a gas oil having an initial boiling point above about 204° C. and an end point of at least about 315° C.

27. The process of claim 18 wherein said feedstock comprises deep cut gas oil, vacuum gas oil, thermal oil, residual oil, cycle stock, whole top crude, tar sand oil, shale oil, or a product of hydrotreatment thereof.

28. The process of claim 18 wherein said catalyst composition further comprises from about 0.01 ppm to about 100 ppm by weight of an oxidation promoter selected from the group consisting of platinum, palladium, iridium, osmium, rhodium, ruthenium, rhenium, and combination thereof.

29. A process for cracking feedstock hydrocarbon compounds to product comprising gasoline and olefins of 3 to 4 carbon atoms which comprises contacting said feedstock at cracking conditions including a temperature of from about 400° C. to about 650° C. with a catalyst composition comprising an active form of crystalline material exhibiting a characteristic X-ray diffraction pattern including d-spacing maxima values as shown in Table I, said crystalline material having been synthesized by a method comprising (i) preparing a mixture capable of forming said material, said mixture comprising sources of alkali metal (M), an oxide of trivalent element (X), an oxide of tetravalent element (Y), water and triquat (R) having a formula $C_{15}H_{39}N_4^{+++}$ and represented as follows:

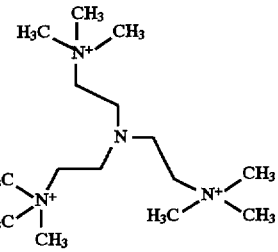

and having a composition, in terms of mole ratios, within the following ranges:

| | |
|---|---|
| YO$_2$/X$_2$O$_3$ | 8 to 30 |
| H$_2$O/YO$_2$ | 8 to 22 |

| | |
|---|---|
| OH⁻/YO$_2$ | 0.4 to 1.1 |
| M/YO$_2$ | 0.2 to 1.3 |
| R/YO$_2$ | 0.03 to 1.2; |

(ii) maintaining said mixture under sufficient conditions including a temperature of from about 110° C. to about 150° C. until crystals of said material are formed; and (iii) recovering said crystalline material from step (ii), said recovered crystalline material containing said R.

30. The process of claim 29 wherein said catalyst composition further comprises a molecular sieve material having pore openings of greater than about 7 Angstroms, said molecular sieve material being selected from the group consisting of zeolites REY, USY, REUSY, dealuminated Y, ultrahydrophobic Y, silicon-enriched dealuminated Y, ZSM-20, Beta, L, silicoalumino-phosphates SAPO-5, SAPO-37, SAPO-40, MCM-9, metallo-aluminophosphate MAPO-36, aluminophosphate VPI-5, and mesoporous crystalline MCM-41.

31. The process of claim 30 wherein said catalyst composition further comprises phosphorus.

32. The process of claim 30 wherein the molecular sieve material comprises REY, USY, or REUSY.

33. The process of claim 29 wherein said feedstock comprises a gas oil having an initial boiling point above about 204° C. and an end point of at least about 315° C.

34. The process of claim 29 wherein said feedstock comprises deep cut gas oil, vacuum gas oil, thermal oil, residual oil, cycle stock, whole top crude, tar sand oil, shale oil, or a product of hydrotreatment thereof.

35. The process of claim 29 wherein said catalyst composition further comprises from about 0.01 ppm to about 100 ppm by weight of an oxidation promoter selected from the group consisting of platinum, palladium, iridium, osmium, rhodium, ruthenium, rhenium, and combination thereof.

36. A process for separating at least one component from a mixture of components in the vapor or liquid phase having differential sorption characteristics with respect to a sorbent comprising a crystalline material exhibiting a characteristic X-ray diffraction pattern including d-spacing maxima values as shown in Table I, said crystalline material having been synthesized by a method comprising (i) preparing a mixture capable of forming said material, said mixture comprising sources of alkali metal (M), an oxide of trivalent element (X), an oxide of tetravalent element (Y), water and triquat (R) having a formula $C_{15}H_{39}N^{+++}$ and represented as follows:

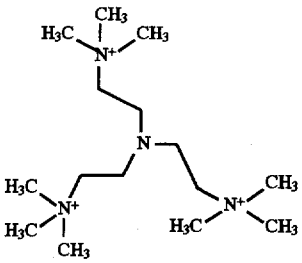

and having a composition, in terms of mole ratios, within the following ranges:

| | |
|---|---|
| YO$_2$/X$_2$O$_3$ | 8 to 30 |
| H$_2$O/YO$_2$ | 8 to 22 |
| OH⁻/YO$_2$ | 0.4 to 1.1 |
| M/YO$_2$ | 0.2 to 1.3 |
| R/YO$_2$ | 0.03 to 1.2; |

(ii) maintaining said mixture under sufficient conditions including a temperature of from about 110° C. to about 150° C. until crystals of said material are formed; and (iii) recovering said crystalline material from step (ii), said recovered crystalline material containing said R, said process comprising contacting the mixture containing said components with said sorbent to selectively sorb from the mixture and onto said sorbent at least one component of the mixture, so as to effect a selective separation of the at least one sorbed component from the remaining at least one unsorbed component of the mixture.

* * * * *

UNITED STATES PATENT AND TRADEMARK OFFICE
CERTIFICATE OF CORRECTION

PATENT NO. : 5,689,024
DATED : November 18, 1997
INVENTOR(S) : KIRK D. SCHMITT

It is certified that error appears in the above-indentified patent and that said Letters Patent is hereby corrected as shown below:

Claim 1, column 17, line 25, "convening" should be

--converting--.

Signed and Sealed this

Seventeenth Day of February, 1998

*Attest:*

BRUCE LEHMAN

*Attesting Officer*　　　*Commissioner of Patents and Trademarks*